(12) United States Patent
Marton et al.

(10) Patent No.: US 9,289,323 B2
(45) Date of Patent: Mar. 22, 2016

(54) ICE BAG WITH AIR RELEASE VALVE FOR THERAPEUTIC TREATMENT

(75) Inventors: Robert Marton, Yorba Linda, CA (US); Anthony Katz, Laguna Niguel, CA (US)

(73) Assignee: Hyper Ice, Inc., Irvine, CA (US)

( * ) Notice: Subject to any disclaimer, the term of this patent is extended or adjusted under 35 U.S.C. 154(b) by 1383 days.

(21) Appl. No.: 12/987,989

(22) Filed: Jan. 10, 2011

(65) Prior Publication Data

US 2012/0031142 A1 Feb. 9, 2012

Related U.S. Application Data

(60) Provisional application No. 61/424,044, filed on Dec. 16, 2010, provisional application No. 61/416,278, filed on Nov. 22, 2010, provisional application No. 61/371,145, filed on Aug. 5, 2010.

(51) Int. Cl.
*B65D 33/01* (2006.01)
*A61F 7/10* (2006.01)
(Continued)

(52) U.S. Cl.
CPC . *A61F 7/10* (2013.01); *A61F 7/103* (2013.01); *A61F 2007/0001* (2013.01); *A61F 2007/0225* (2013.01); *A61F 2007/0228* (2013.01); *A61F 2007/105* (2013.01)

(58) Field of Classification Search
CPC ..... A61F 7/10; A61F 7/103; A61F 2007/105; B65D 33/16; B65D 41/28; B65D 47/20; B65D 47/32; B65D 47/121; B65D 47/245
USPC ............ 383/44, 45; 220/203.01, 203.29, 202, 220/203.04, 203.13, 203.11; 607/108, 112, 607/114; 215/260, 270
See application file for complete search history.

(56) References Cited

U.S. PATENT DOCUMENTS 1,743,244 A * 1/1930 Shulman ........................ 126/403
2,435,637 A * 2/1948 Sevush .......................... 604/408
(Continued)

FOREIGN PATENT DOCUMENTS

DE 8902442 U1 * 3/1989 ................ A61F 7/08
DE 8902442 U1 4/1989
(Continued)

OTHER PUBLICATIONS

Van Loon-MeGard, Veronique, Authorized Officer of the European Patent Office, "Notification of Transmittal of the International Search Report and the Written Opinion of the International Searching Authority, or the Declaration," mailed on Oct. 19, 2011, for International Patent Application No. PCT/US2011/046612, filed on Aug. 4, 2011.
(Continued)

*Primary Examiner* — Linda Dvorak
*Assistant Examiner* — Yasamin Ekrami
(74) *Attorney, Agent, or Firm* — Jerry Turner Sewell

(57) ABSTRACT

A system simultaneously applies compression and cooling to a body part. An ice bag has a removable cap for inserting ice and removing water. An air release valve in the cap allows release of air from the ice bag without removing or loosening the cap. A compression wrap is a unitary sheet of elastic material having a central body with straps extending therefrom. A hole in the central body receives the neck of the ice bag, which is positioned over the body part. The unitary body and straps of the sheet apply pressure via the ice bag. Air released into the ice bag from melting ice is removed via the air release valve without disturbing the compression wrap or the cap. The compression wrap contracts to compensate for the volume of the released air, thus maintaining continuous pressure on and thermal contact with the body part.

11 Claims, 12 Drawing Sheets

(51) Int. Cl.
*A61F 7/00* (2006.01)
*A61F 7/02* (2006.01)

(56) References Cited

U.S. PATENT DOCUMENTS

| | | | | |
|---|---|---|---|---|
| 2,603,218 | A * | 7/1952 | Rane | 215/247 |
| 4,136,796 | A * | 1/1979 | Dubois et al. | 220/259.4 |
| 4,505,312 | A * | 3/1985 | Lardner et al. | 141/326 |
| 4,585,003 | A | 4/1986 | Meistrell | |
| 4,675,347 | A * | 6/1987 | Mochizuki et al. | 523/122 |
| 4,685,442 | A * | 8/1987 | Cieslak | 126/204 |
| 4,805,620 | A | 2/1989 | Meistrell | |
| 4,976,262 | A * | 12/1990 | Palmacci | 607/108 |
| 5,090,409 | A | 2/1992 | Genis | |
| 5,230,335 | A * | 7/1993 | Johnson et al. | 607/104 |
| 5,255,390 | A * | 10/1993 | Gross et al. | 2/458 |
| 5,369,807 | A * | 12/1994 | Cho et al. | 2/159 |
| 5,441,533 | A * | 8/1995 | Johnson et al. | 607/104 |
| 5,957,317 | A * | 9/1999 | Lee | 220/212 |
| 5,979,688 | A * | 11/1999 | Stodd | 220/231 |
| 6,056,985 | A * | 5/2000 | Fluckiger et al. | 426/392 |
| 6,789,690 | B2 * | 9/2004 | Nieh et al. | 220/231 |
| 7,959,588 | B1 * | 6/2011 | Wolpa | 602/13 |
| 8,709,058 | B1 * | 4/2014 | Harsy | 607/108 |
| 2002/0092858 | A1 * | 7/2002 | Bowman | 220/709 |
| 2002/0138121 | A1 * | 9/2002 | Fox | 607/96 |
| 2005/0049661 | A1 * | 3/2005 | Koffroth | 607/108 |
| 2006/0163284 | A1 * | 7/2006 | Karl et al. | 222/175 |
| 2006/0282140 | A1 * | 12/2006 | Schock et al. | 607/108 |
| 2007/0161932 | A1 * | 7/2007 | Pick et al. | 602/5 |
| 2007/0292054 | A1 | 12/2007 | Chang | |
| 2008/0086063 | A1 * | 4/2008 | Baxter et al. | 601/46 |
| 2009/0078709 | A1 * | 3/2009 | Murrer, III | 220/592.2 |
| 2011/0009931 | A1 * | 1/2011 | Hong | 607/112 |
| 2011/0052098 | A1 * | 3/2011 | Chang | 383/3 |

FOREIGN PATENT DOCUMENTS

| | | |
|---|---|---|
| GB | 2199252 A | 7/1988 |
| GB | 2276675 A | 9/1994 |
| JP | S06-006100 U | 5/1931 |
| JP | S60-4454 U | 1/1985 |
| JP | S63-311954 A | 12/1988 |

OTHER PUBLICATIONS

Cornelissen, P., Communication pursuant to Article 94(3) EPC for European Application No. 11 746 089.9, Jan. 14, 2014.

Jul. 14, 2015 Notice of Rejection of Japanese Application No. 2013-523338.

Informal English Translation of Jul. 14, 2015 Notice of Rejection of Japanese Application No. 2013-523338.

* cited by examiner

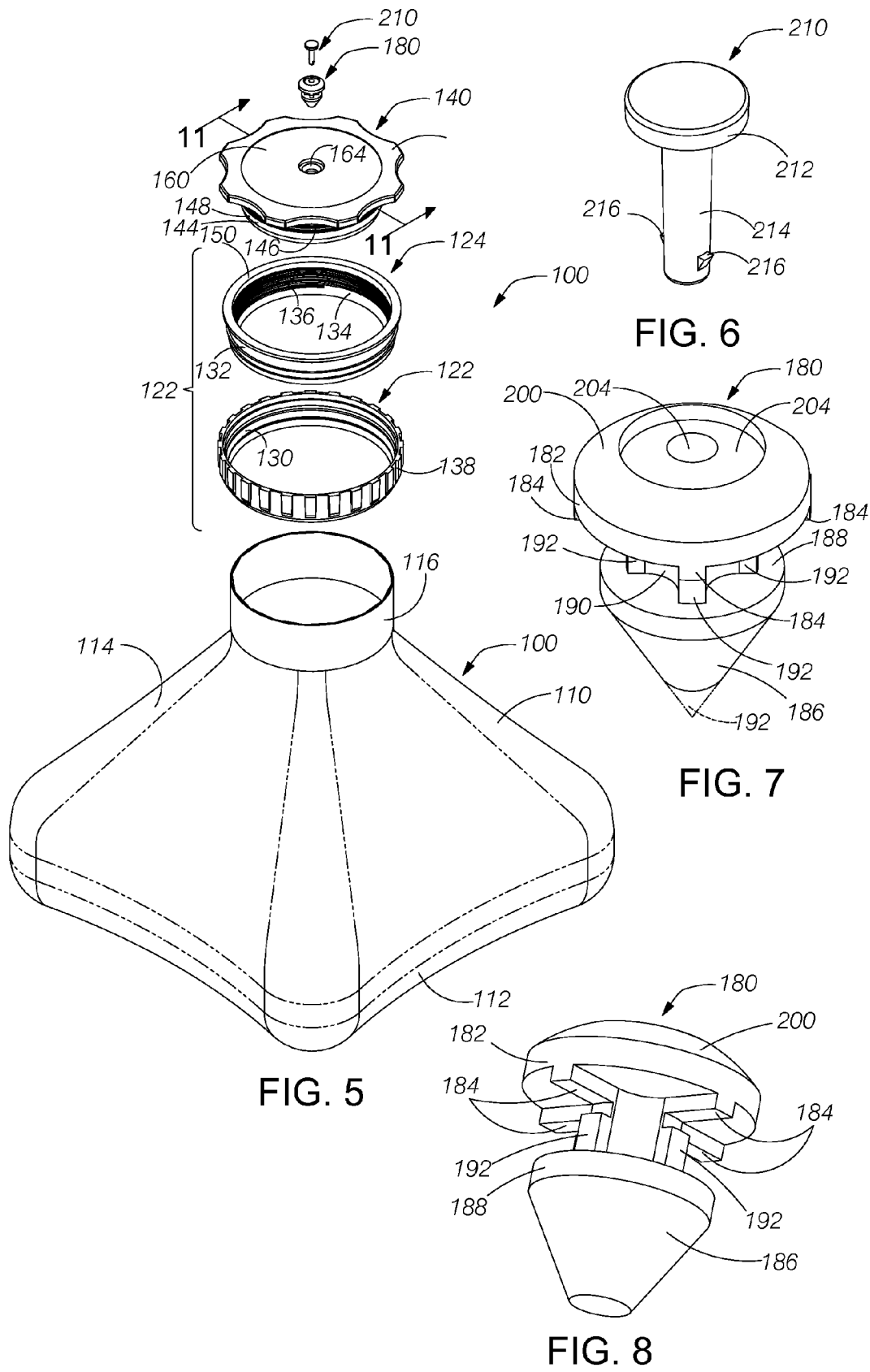

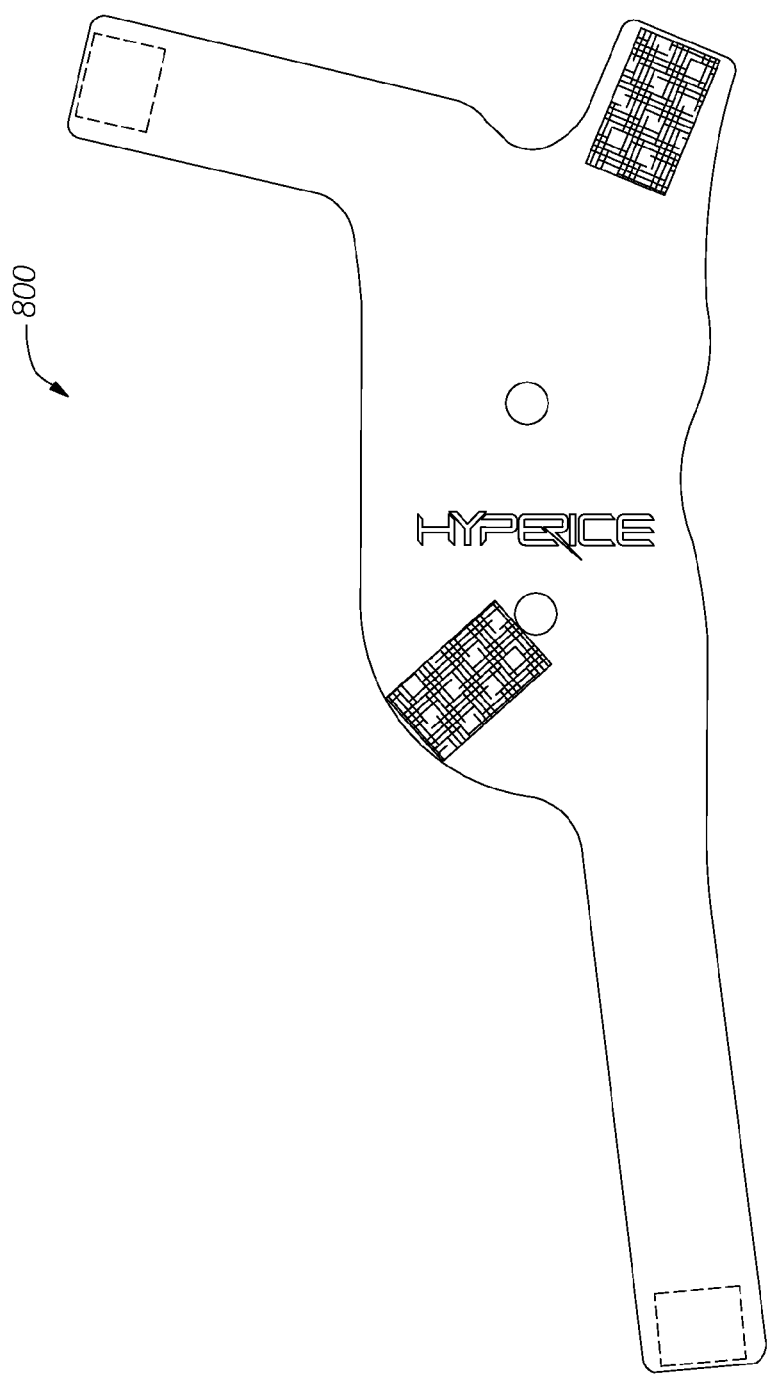

ICE BAG WITH AIR RELEASE VALVE FOR THERAPEUTIC TREATMENT

RELATED APPLICATIONS

The present application claims the benefit of priority under 35 USC §119(e) to U.S. Provisional Application No. 61/371,145, filed on Aug. 5, 2010, to U.S. Provisional Application No. 61/416,278, filed on Nov. 22, 2010, and to U.S. Provisional Application No. 61/424,044, filed on Dec. 16, 2010.

BACKGROUND OF THE INVENTION

1. Field of the Invention

The present invention is in the field of ice bags to apply against a portion of a body to remove heat from the body for therapeutic treatment.

2. Description of the Related Art

An ice bag (referred to as a cryotherapy device) is commonly applied to a portion of a body to remove heat from the body as part of a therapeutic treatment for sore and inflamed muscles and other tissues. In particular, the combination of rest, ice, compression and elevation is a treatment method that is most widely used for a soft tissue injury. Ideally, the ice bag is held securely against the treated body portion to provide secure contact over a large area so that heat is transferred from the body portion to the ice in the ice bag. A compression wrap is often used in combination with the ice bag to provide the secure contact and to also apply pressure to the body portion to enhance the treatment process.

Applicants have found that as the ice in a conventional ice bag melts, the air trapped in the ice is released into the cavity of the ice bag and reduces the effectiveness of the compression since the compression wrap is applying pressure via the compressible air in the bag rather than solely via the incompressible ice and water that originally filled the ice bag. Although a conventional ice bag can be partially opened by partially unscrewing the filling cap to release a portion of the air in the ice bag, this procedure has been found to be difficult to accomplish without risking release of a portion of the water in the ice bag. Furthermore, the person being treated may not be able to unscrew threaded filling cap when the ice bag is located on a shoulder or other difficult to reach body portion. Thus, Applicants have determined that the conventional ice bag is unsatisfactory, and that a need thus exists for an improved ice bag for use with a compression wrap for therapeutic treatment in order to increase the depth of penetration of cold into the body portion being treated.

SUMMARY OF THE INVENTION

An aspect of embodiments in accordance with the present invention is a system that simultaneously applies compression and cooling to a body part. An ice bag has a removable cap for inserting ice and removing water. An air release valve in the cap allows release of air from the ice bag without removing or loosening the cap. A compression wrap is a unitary sheet of elastic material having a central body with straps extending therefrom. A hole in the central body receives the neck of the ice bag, which is positioned over the body part. The unitary body and straps of the sheet apply pressure via the ice bag. Air released into the ice bag from melting ice is removed via the air release valve without disturbing the compression wrap or the cap. The compression wrap contracts to compensate for the volume of the released air, thus maintaining continuous pressure on and thermal contact with the body part.

Another aspect of embodiments in accordance with the present invention is an ice bag for therapeutic treatment for use in combination with a compression wrap comprises a flexible bag having a cavity accessible via a neck portion. Preferably, the flexible bag comprises latex, silicone or other suitable material. Preferably, the flexible bag comprises a blend of medical grade (hypoallergenic) latex and an antimicrobial solution. Preferably, the flexible bag is sufficiently thin to provide rapid heat transfer from a portion of the body to which the ice bag is applied to ice within the ice bag. In the illustrated embodiment, the flexible bag has a main, box-shaped body portion that is generally rectangular (e.g., a square in one embodiment) that tapers to a generally circular neck portion. The neck portion of the flexible bag is secured to a circular, threaded connector that receives a removable cap. The threaded connector has a sufficient diameter to allow ice to be easily inserted through the opening in the uncapped connector. For example, in one embodiment, the opening through the connector into the neck of the flexible bag has a diameter generally corresponding to the diameter of a conventional drinking glass (e.g., approximately 2.75 inches). Thus, for example, the flexible bag can be filled from a conventional ice dispenser on or in a refrigerator or other ice source. Once the ice bag is filled, the removable cap is threaded into secure engagement with the connector to seal the ice bag to prevent leakage of water from the ice bag as the ice melts within the bag.

Unlike the caps of conventional ice bags, the removable cap of the ice bag disclosed herein has an air valve positioned on the outer surface of the cap. The air valve is held in a closed position by the elasticity of the air valve and by any pressure with the ice bag. The air valve is easily pushed by a user to open sufficiently to allow air to be released from the ice bag, both when the ice bag is initially filled with ice and when additional air is released from melting ice. The air valve is constructed to open by only a very small amount to release air without releasing any significant amount of water. After releasing the air in the ice bag, the neck of the ice bag is positioned through an opening in a compression wrap and then positioned on the body portion to be treated with the main body portion of the ice bag against the body portion and with the neck portion extending through the opening in the compression wrap so that the cap is accessible by a user. The compression wrap is then tightened to apply pressure to the ice bag against the body portion and any additional air in the ice bag is released using the air valve. As the treatment continues and air is released from the ice within the ice bag, the person being treated or another person only has to touch the air valve gently to allow air to escape from the ice bag so that the compression wrap is able to apply pressure directly against the ice within the ice bag and thereby maintain pressure against the body portion being treated.

The air valve comprises a compressible plug that fits within a hole formed in the removable cap. The compressible plug includes an inner flange and an outer flange. Once positioned within the hole in the cap, the inner flange of the compressible plug statically engages the inner surface of the cap and blocks the release of air and water from the ice bag. The air valve further comprises an air release button that fits in blind bore having a closed end within the compressible plug. The air release button is movable against the closed end of the blind bore to move the inner flange of the compressible plug away from the inner surface of the cap thereby providing an opening between the inner flange and the cap to allow air within the ice bag to escape from the ice bag. When the ice bag is under pressure from the compression wrap or from pressure applied by a user, air within the ice bag is forced from the ice bag through the air valve so that the interior of the bag comprises mostly water and ice.

BRIEF DESCRIPTION OF THE DRAWINGS

Embodiments in accordance with aspects of the present invention are described below in connection with the attached drawings in which:

FIG. 5 illustrates an exploded perspective view of the ice bag of FIG. 1;

FIG. 6 illustrates an enlarged perspective view of the air release button of FIG. 4;

FIG. 7 illustrates an enlarged perspective view of the air release valve of FIG. 4;

FIG. 8 illustrates a perspective view of the air release valve of FIG. 7 rotated to show the rib structure beneath the upper portion of the valve;

FIGS. 17A and 17B illustrate the application of two ice bags to a person's left shoulder using the compression wrap of FIG. 16 wherein FIG. 17A illustrates a front view and FIG. 17B illustrates a rear view;

FIG. 18 illustrates a plan view of a compression wrap for securing a first ice bag of FIGS. 1-11 to the front of a person's right shoulder and for securing a second ice bag of FIGS. 1-11 to the back of the person's right shoulder.

DETAILED DESCRIPTION OF PREFERRED EMBODIMENTS

Figure 1:
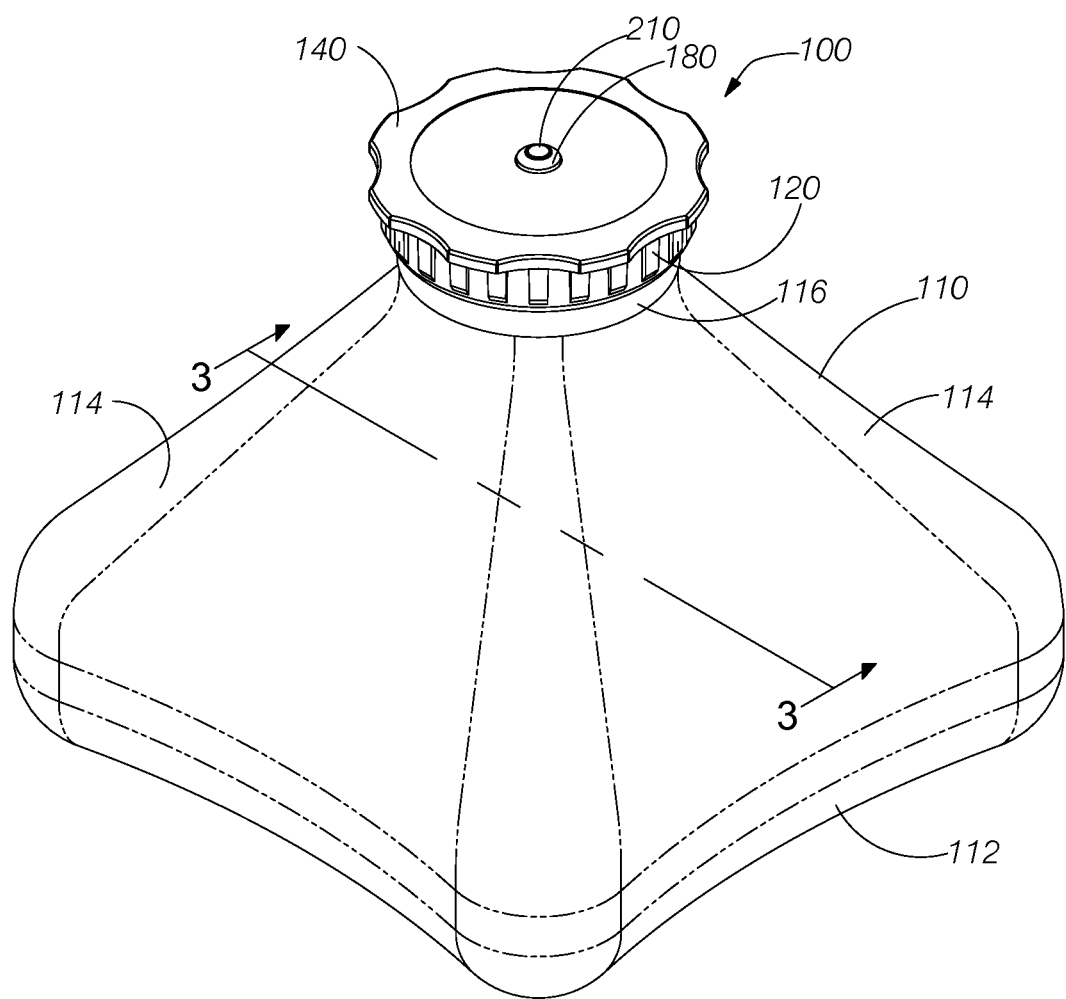
FIG. 1 illustrates a perspective view of an ice bag in accordance with embodiments of the invention.
Figure 2:
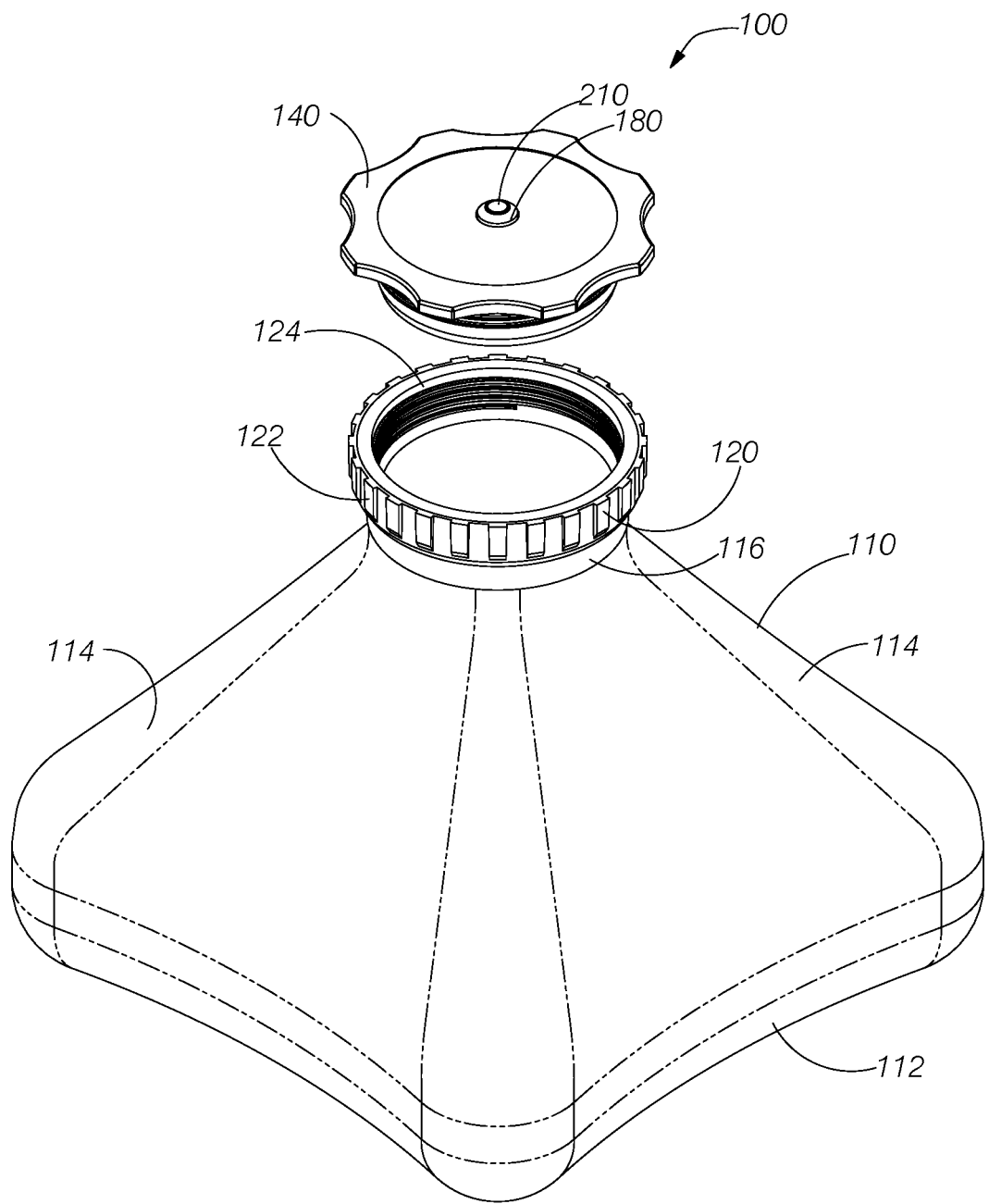
FIG. 2 illustrates a perspective view of the ice bag of FIG. 1 with the cap removed so that ice can be added to the ice bag or water removed from the ice bag.
Figure 3:
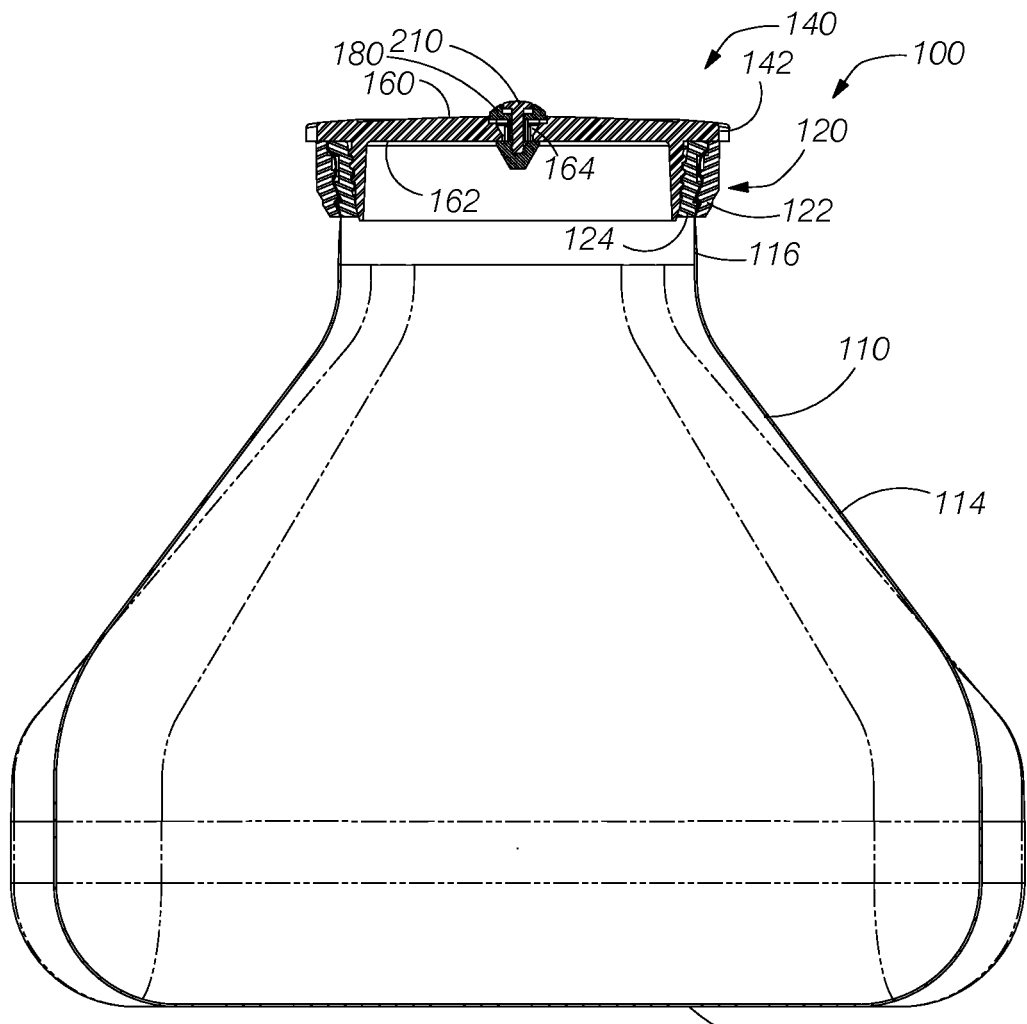
FIG. 3 illustrates an elevational cross-sectional view of the ice bag of FIG. 1 taken along the section line 3-3 in FIG. 1.

The ice bag system and compression wrap system is disclosed herein with respect to exemplary embodiments. The embodiments are disclosed for illustration of the fastening system and are not limiting except as defined in the appended claims.

FIGS. 1-11 illustrate an ice bag 100 in accordance with an exemplary embodiment of the invention. The ice bag comprises a lower, box-like main body portion 110. In the illustrated embodiment, the body portion has a generally square bottom portion 112, which transitions to a generally four-sided pyramidal-shaped upper portion 114. The upper portion transitions (tapers inwardly) to a cylindrical neck portion 116. The square shape of the bottom portion provides more surface area for placement against a body portion of a person being treated with cold and compression therapy. The ice bag preferably comprises latex or other suitable flexible waterproof material. In one embodiment, the ice bag comprises silicone, such as, medical grade silicone. In a particularly preferred embodiment, the ice bag comprises a blend of medical grade (hypoallergenic) latex and an antimicrobial solution. For example, in one embodiment, the latex material is processed by leaching to remove antigens (proteins) that can cause allergic reactions. The antimicrobial solution is added to the blend to inhibit the growth of bacteria, mold, fungi and other microbes to provide a sanitary ice bag. In the illustrated embodiment, the latex (or other suitable material) has a thickness that is selected to be sufficiently thin to provide a high temperature transfer rate. For example, in the illustrated embodiment, the material has a thickness of 0.015 inch (15 mils). Thus, heat from the portion of the body to which the ice bag is applied is rapidly transferred to the ice within the ice bag to cool the portion of the body in a more effective manner than thicker ice bag materials on the market.

Figure 4:
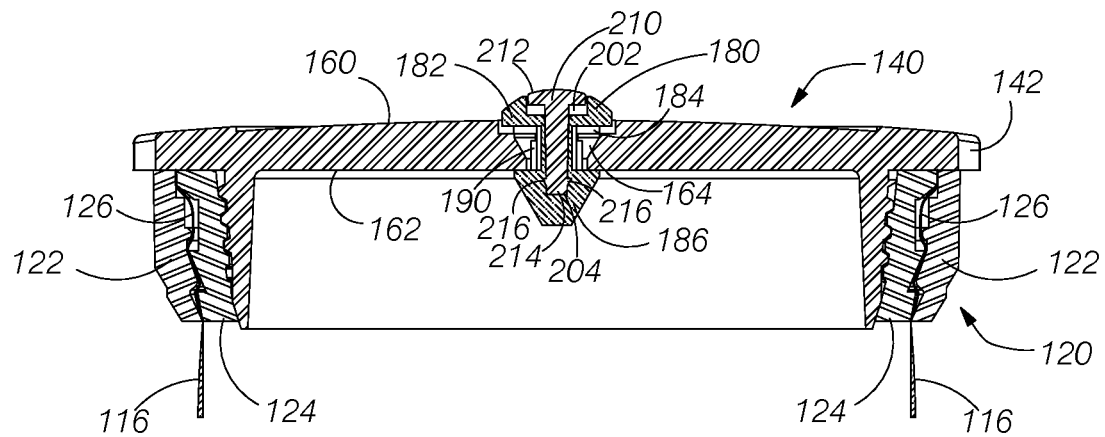
FIG. 4 illustrates an enlarged elevational view of the neck of the ice bag, the connector and the cap of FIG. 3.

The cylindrical neck portion 116 of the main body portion 110 of the ice bag 100 is terminated in a female threaded connector 120. As shown in more detail in the cross-sectional views of FIGS. 3 and 4 and the exploded view of FIG. 5, the connector comprises an outer collar ring 122 and an inner receiver ring 124. The outer collar ring is positioned around the outside of the neck of the ice bag, and the inner receiver ring is positioned inside the neck of the ice bag. As shown in FIG. 4, the outer collar ring and the inner receiver ring are forced together to secure an upper portion 126 of the neck of the ice bag between the two rings so that the two rings form the female connector. A inner surface 130 of the outer collar ring and an outer surface 132 of the inner receiver ring have mating ridges so that connector cannot be readily removed from the upper portion of the neck of the ice bag and so that the a secure watertight seal is formed between the neck of the ice bag and the connector.

The inner receiver ring 124 of the female threaded connector 120 includes an inner cylindrical bore 134 that includes a female thread 136 formed thereon. The outer collar ring has a ridged outer surface 138 that is easy to grip.

The female threaded connector 120 receives a cap 140. The cap comprises an upper gripping portion 142 and a lower engagement portion 144. The lower engagement portion is cylindrical and has a male thread 146 formed on an outer surface 148. The male thread engages the female thread 132 of the inner receiver ring 124 so that the cap is securable to the female threaded connector. The upper gripping portion of the cap and the ridged outer surface 134 of the outer collar ring enable a user to securely engage the cap with the inner receiver ring. A flange 150 on the outer perimeter of the cap also firmly engages a top surface 152 of the inner receiver ring. The engagement of the threads and the engagement of the flange with the top surface form a waterproof seal between the cap and the inner receiver ring. Thus, any water that forms in the ice bag when ice melts is prevented from leaking from the ice bag.

Figure 9:
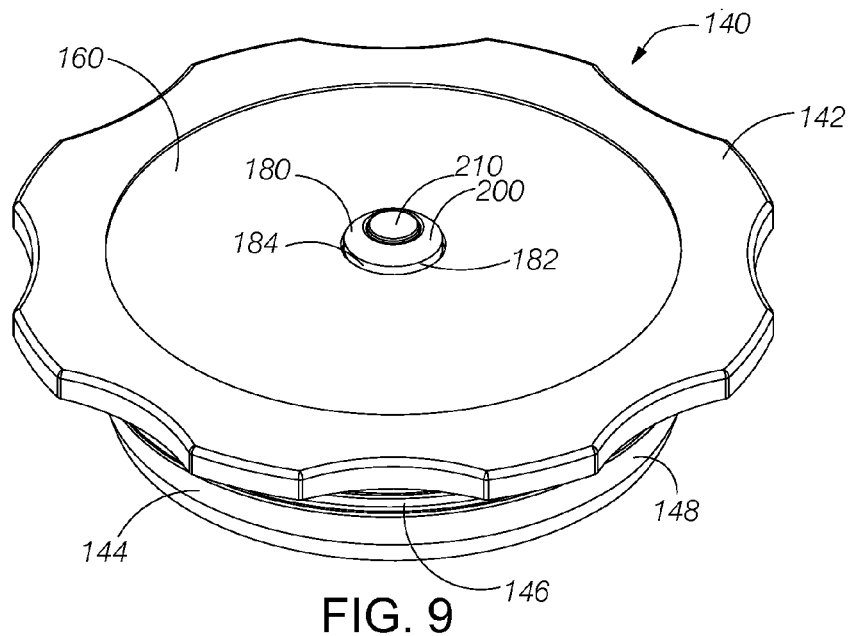
FIG. 9 illustrates an enlarged perspective view of the top of the cap of FIG. 4 showing the air release valve and air release button extending from the outer (top) surface of the cap.
Figure 10:
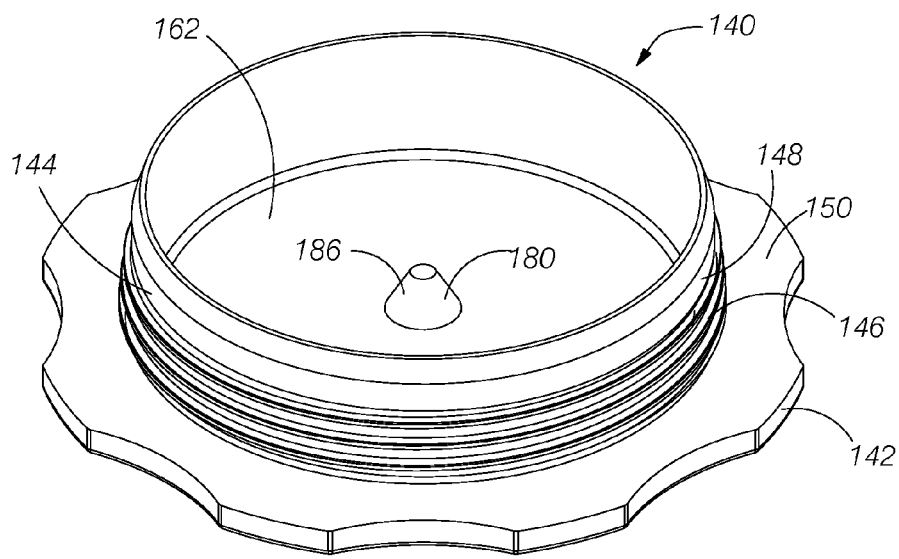
FIG. 10 illustrates an enlarged perspective view of the bottom of the cap of FIG. 4 showing the extension of the air release valve through the inner (bottom) surface of the cap.
Figure 11:
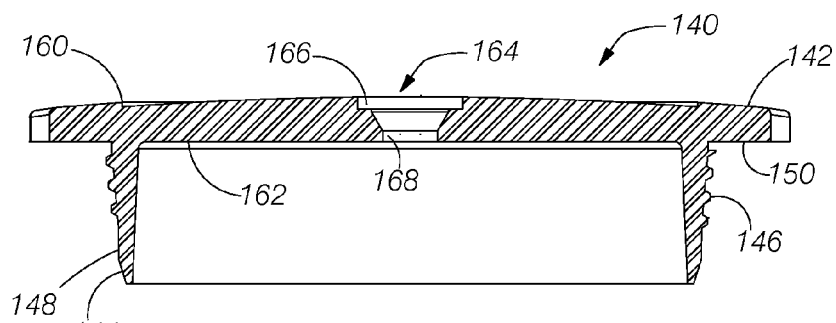
FIG. 11 illustrates an elevational cross-sectional view of the cap of FIG. 5 taken along the section line 11-11 in FIG. 5.

As shown in more detail in FIGS. 9 and 10, the upper gripping portion 142 of the cap 140 has an upper (outer) surface 160 and a lower (inner) surface 162. The upper gripping portion is perforated with a hole 164 (FIG. 5) that is generally centered with respect to the upper surface. As shown in more detail in the cross-sectional view of FIG. 11, the hole has multiple diameters. A first portion 166 of the hole proximate to the upper surface has a larger diameter (e.g., 0.48 inch) and extends to a depth of approximately 0.115 inch. The hole tapers inward below the first portion so that a second portion 168 of the hole proximate the lower surface has a smaller diameter of approximately 0.25 inch.

The hole 164 of the upper gripping portion 142 of the cap 140 receives an air release valve 180, which is shown in enlarged detail in FIGS. 7 and 8. A generally disk-shaped upper portion 182 of the air release valve has a diameter sized to fit within the first (upper) portion of the hole between the outer circumference of the upper portion of the air release valve and the inner circumference of the upper portion of the hole, as shown in FIG. 9. As shown in FIG. 8, the lower surface of the upper portion of the air release valve includes a plurality of ribs 184 that form an X-shaped pattern. The gaps between the ribs provide a fluid communication path beneath the upper portion of the air release valve to the clearance around the upper portion of the air release valve.

The air release valve 180 further includes a generally cone-shaped lower portion 186, which is inverted so that the lower portion has an upper base 188. The upper base of the lower portion is sized to be larger than the second (lower) portion 168 of the hole 164. A middle portion 190 of the air release valve extends between the upper portion and the base of the lower portion. As illustrated in FIGS. 7 and 8, the middle portion preferably has a generally X-shaped cross section with fillets between bars 192 that form the X shape.

The cone-shaped lower portion 186 of the air release valve 180 is forced through the second portion 168 of the hole 164 of the upper gripping portion 142 of the cap 140. The extended length of the lower portion of the air release valve is grippable by a manual or automated tool so that the lower portion can be pulled through the hole sufficiently far that the upper base 186 of the lower portion passes entirely through hole. The elastic material of the air release valve allows the upper base to compress sufficiently to pass through the hole. Once pulled through the hole, the upper base expands so that the air release valve cannot be removed from the hole. In the preferred embodiment, the length of the middle portion 190 of the air release valve is selected to be less than the distance from the bottom of the first portion 166 of the hole to the lower surface 162 of the upper gripping portion. Accordingly, the middle portion of the air release valve is stretched when the air release valve is inserted in the hole. After the air release valve is inserted, the middle portion retracts toward the original length and forces the upper base of the lower portion against the lower surface of the upper gripping portion. Accordingly, the middle portion functions as a biasing spring to hold the base of the lower portion against the lower surface of the cap. The base of the lower portion thus functions as a flange that precludes removal and that also seals the second portion of the hole as shown in FIG. 10. As indicated above, the middle portion has a generally X-shaped cross section. The X-shaped cross section reduces the material that must be stretched during the installation process and also reduces the pressure required to operate the air release valve in the manner described below. After installation, a lower portion 192 (FIG. 7) of the air release valve is removed to truncate the cone shape as shown in FIG. 8.

As shown in more detail in FIG. 7, the disk-shaped upper portion 182 of the air release valve 180 has a generally convex upper surface 200. The upper surface has a round recess 202 that has a depth of approximately 0.125 inch. A blind central bore 204 extends downwardly from the bottom of the recess to a depth of approximately 0.325 inch.

The air release valve 180 receives an air release button 210 having a disk-shaped upper portion 212 sized to fit into the round recess 202 and having an extended cylindrical lower portion 214 sized to fit into the blind central bore 204. In particular, the cylindrical lower portion of the air release button extends approximately 0.37 inch below the disk-shaped portion and is tapered (approximately 1 degree) inwardly. The lower portion of the air release button includes a pair of diametrically opposed barbs 216. After installing the air release valve in the cap 140, the air release button is inserted into round recess and the central bore of the air release valve as shown in the cross-sectional view of FIG. 4. The two barbs hinder or prevent the removal of the air release button after installation.

As shown in FIG. 4, the upper portion 212 of the air release button 210 is displaced from the bottom of the recess 202 of the air release valve 180. When the air release button is pushed, the upper portion of the air release button moves downward within the recess; however, the lower end of the extended lower portion 214 pushes against the bottom of the blind central bore 204 of the air release valve. Because of the reduced cross section of the middle portion 190 of the air release valve, the middle portion functions as a spring that stretches to allow the top 188 of the cone-shaped lower portion 186 of the air release valve to move away from the lower (inner) surface 162 of the cap 140, thus opening a small gap (not shown) that allows air to be released from the ice bag 100. The spacing between the elements of the X-shaped cross section of the middle portion allows the air to flow through the hole 164, and the spacing between the ribs 184 allows the air to flow below the upper portion 182 to the clearance around the upper portion and to thereby flow out of the top portion of the hole. The gap formed between the air release valve and the lower surface of the cap is sufficiently small that little or no water is released from the ice bag. Furthermore, the intended use of the ice bag will not cause water to be near the air release valve to be released through the gap. The elastic material of the air release valve requires very little pressure on the top of the air release button to form a gap sufficient to release air from the ice bag. When pressure is released from the top of the air release button, middle portion of the air release valve again functions as a spring to force the top of the cone-shaped bottom portion against the inner surface of the cap to again seal the hole.

Figure 12:
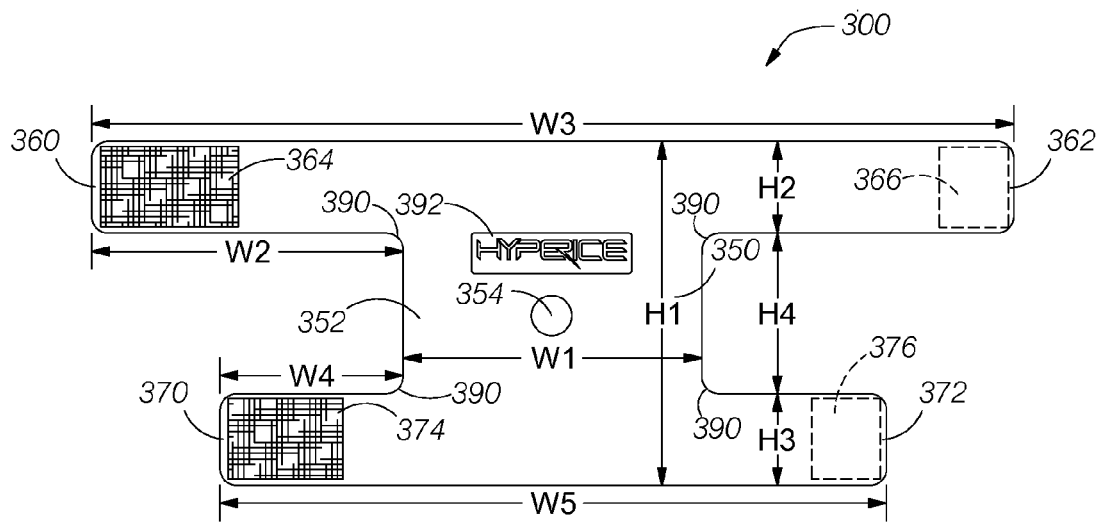
FIG. 12 illustrates a plan view of a compression wrap for securing the ice bag of FIGS. 1-11 to a person's hip.
Figure 13:
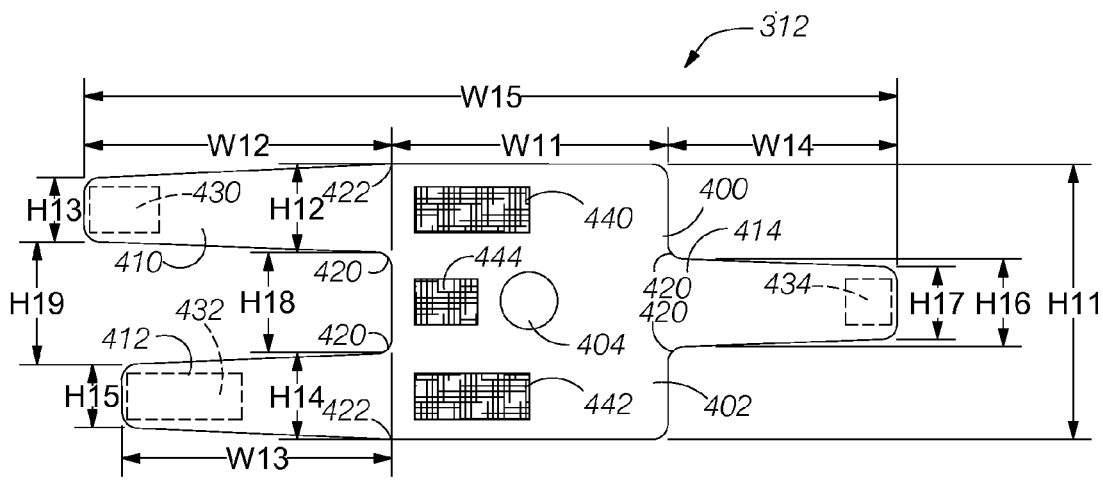
FIG. 13 illustrates a plan view of a compression wrap for securing the ice bag of FIGS. 1-11 to a person's knee.

The ice bag 100 shown in FIGS. 1-11 is advantageously used with improved compression wraps shown in FIGS. 12-18. In particular, FIG. 12 illustrates a compression wrap 300 for securing the ice bag to a person's hip. FIG. 13 illustrates a compression wrap 310 for securing the ice bag to a person's knee. FIGS. 14-18 illustrate embodiments of shoulder compression wraps.

The hip compression wrap 300 of FIG. 12 comprises a continuous sheet 350 of commercially available L-foam neoprene (polychlorphene (CR) foam), or a material with similar properties. The sheet is strong, soft and elastic (stretchable). The sheet has a thickness of approximately 2 millimeters. The sheet is shaped to have a pattern comprising a generally rectangular central body portion 352 having a width W1 and a height H2. As used herein, the "width" refers to the horizontal dimension and the "height" refers to the vertical dimension when the compression wrap is oriented as shown in FIG. 12.

A hole 354 is formed through the central body portion 352 approximately at the center. In the illustrated embodiment, the hole has a diameter of approximately 1.75 inches.

Four securing straps extend from the central body portion 352. A first strap 360 extends to the left from the top of central body portion, and a second strap 362 extends to the right from the top of the central body portion. Each of the first strap and the second strap has a respective width W2 and a respective height H2. The upper edges of the first strap and the second strap are aligned with the upper edge of the central body portion so that the overall width of the sheet 350 from the left end of the first strap to the right end of second strap is W3, where W3 is equal to W1+(2×W2).

The exposed surface of the first strap 360 has a generally rectangular section 364 of the loop (fuzzy) portion of a hook and loop fastening system positioned proximate to the left end. The rectangular section of the loop portion is secured thereon by gluing, by stitching or by another suitable method. The obverse (unexposed side) of the second strap 362 has a generally rectangular section 366 (shown in hidden lines) of the hook portion of a hook and loop fastening system proximate the right end. The rectangular section of the hook portion is secured thereon by a suitable method. In the illustrated embodiment, the rectangular section of the loop portion on the first strap is wider than the rectangular section of the hook portion on the second strap to allow the engagement to be adjusted, as discussed below. An exemplary suitable hook and loop fastening system is a VELCRO® brand fastening system available from Velcro USA Inc.; however, hook and loop fastening systems from other manufacturers may also be used.

A third strap 370 extends to the left from the bottom of the central body portion 352, and a fourth strap 372 extends to the right from the bottom of the central body portion. Each of the third strap and the fourth strap has a respective width W4 and a respective height H3. The lower edges of the third strap and the fourth strap are aligned with the upper edge of the central body portion so that the overall width of the sheet 350 from the left end of the third strap to the right end of fourth strap is W5, where W5 is equal to W1+(2×W4).

The exposed surface of the third strap 370 has a generally rectangular section 374 of the loop portion of a hook and loop fastening system positioned proximate the left end. The rectangular section of the loop portion is secured thereon by gluing, by stitching or by another suitable method. The obverse (unexposed side) of the fourth strap 372 has a generally rectangular section 376 (shown in hidden lines) of the hook portion of a hook and loop fastening system positioned proximate the right end. The rectangular section of the hook portion is secured thereon by a suitable method. In the illustrated embodiment, the rectangular section of the loop portion on the third strap is wider than the rectangular section of the hook portion on the fourth strap to allow the engagement to be adjusted, as discussed below.

The lower edges of the first strap 360 and the second strap 362 are spaced apart from the upper edges of the third strap 370 and the fourth strap 372, respectively, by a height H4. Accordingly, the overall height H1 of the main body portion is substantially equal to the sum of the heights H2, H3 and H4.

The dimensions of the hip compression wrap 310 can be varied in accordance with ranges of sizes of persons for whom the hip compression wrap is intended. For example, in one exemplary embodiment, the widths and heights have the following approximate dimensions: W1≈13 inches; W2≈13.5 inches; W3≈40 inches; W4≈8 inches; W5≈29 inches; H1≈15 inches; H2≈4 inches; H3≈4 inches; and H4≈7 inches.

As illustrated in FIG. 12, the four straps of the hip compression wrap 300 are generally perpendicular to the central body portion 352. Preferably, the perpendicular intersections the central body portion with the lower edges of the first strap 360 and the second strap 362 and with the upper edges of the third strap 370 and the fourth strap 372 are rounded to form fillets 390. The fillets function to inhibit tearing of the sheet 350 when the straps and the central body portion are stretched as discussed below. Preferably, the outer vertices of the four straps are also rounded.

Preferably, the outer edges forming the outer boundaries of the straps 360, 362, 370, 372 and the central body portion 352 of the sheet 350 of the hip compression wrap and the inner edge of the sheet defining the hole 354 are reinforced by trimming the edges with elastic webbing (not shown), which is commercially available from a number of sources. The elastic webbing is sewn to the sheet proximate the edges in a conventional manner using elastic thread, which is also commercially available.

In the illustrated embodiment, the central body portion 352 has an optional identification label 392 formed thereon.

When used to provide pressure to the ice bag 100 placed on a person's hip, the neck portion 116 of the ice bag is pushed through the hole 354 in the central body portion 352. The elasticity of the sheet 350 allows the hole to stretch to accommodate the slightly larger diameter of the neck portion and to retain the neck portion securely therein. After filling the ice bag with ice, the cap 140 is secured to the threaded connector 120. The air release button 210 is initially depressed and pressure is applied to the ice bag to remove a substantial portion of any air that entered the bag while the cap was opened. The generally square bottom portion 112 of the ice bag is then positioned against the person's hip. The first strap 360 and the second strap 362 are extended around the waist of the person with the loop section 364 on the first strap positioned beneath the hook section 366 on the second strap. The lengths of the first strap and the second strap are preferably selected so that both straps are stretched to extend around the waist. After adjusting the positions of the first and second straps, the hook section is engaged with the loop section to secure the two straps to the person's waist.

After securing the first strap 360 and the second strap 362 at the person's waist, the central body portion 350 is stretched downward to position along the outside of the person's hip. The third strap 370 and the fourth strap 372 are stretched around the person's leg below the hip with the loop section 374 of the third strap positioned beneath the hook section 376 of the fourth strap. After adjusting the positions of the third and fourth straps, the hook section is engaged with the loop section to secure the two straps to the person's leg.

The hip compression wrap 300 applies pressure to the ice bag 100. As the ice within the ice bag melts, which reduces the total volume of ice and water within the ice bag, the elasticity of the compression wrap causes the compression wrap to continue to force the ice bag against the person's hip. As the ice melts and releases entrapped air into the ice bag, the air may provide a cushioning effect to reduce the force applied against the hip. The air within the bag is easily removed by pressing on the air release button 210 on the exposed cap 140. As the air is released from the ice bag, the elasticity of the compression wrap maintains the pressure on the hip so that ice remains in thermal contact with the hip through the wall of the ice bag.

The knee compression wrap 312 of FIG. 13 functions similarly to the hip compression wrap 310 and comprises a sheet 400 of L-foam neoprene as described above, or a similar material. The shape of the neoprene sheet is configured for the knee of a person. In particular, a central body portion 402 of the sheet has a width W11 and a height H11. A hole 404 is formed at the approximate center of the central body portion. The hole in the knee compression wrap has a diameter similar to the diameter of the hole in the hip compression wrap, which is approximately 1.75 inches.

Three straps extend generally perpendicularly from the central body portion 402 of the knee compression wrap 312. A first strap 410 extends to the left from the left side of the central body portion proximate to the top of the central body portion and has a width W12. A second strap 412 extends to the left from the left side of the central body portion proximate to the bottom of the central body portion and has a width W13. A third strap 414 extends to the right from the right side of the central body portion and is generally centered with respect to the right side of the central body portion. The third strap has a width W14. The knee compression wrap has an overall width W15, which is the sum of the width W11 of the central body portion, the width W12 of the first strap and the width W14 of the third strap. In the illustrated embodiment, the width W13 of the second strap is shorter than the width W12 of the first strap.

In the illustrated embodiment of the knee compression wrap 312, the three straps are tapered. The first strap 410 has a height H12 at the intersection with the left side of the central body portion 402 and tapers to a height H13 at the left end. The second strap 412 has a height H14 at the intersection with the left side of the central body portion and tapers to a height H15 at the left end. The third strap 414 has a height H16 at the intersection with the right side of the central body portion and tapers to a height H17. The first strap and the second strap are spaced apart by a height H18 at the left side of the central body portion. The respective left ends of the first strap and the second strap are spaced apart in a vertical direction by a height H19. Note however that the left ends of the two straps are not aligned.

The dimensions of the knee compression wrap 312 can be varied in accordance with ranges of sizes of persons for whom the knee compression wrap is intended. For example, in one exemplary embodiment, the widths and heights have the following approximate dimensions: W11≈8.5 inches; W12≈9.5 inches; W13≈8.25 inches; W14≈7 inches; W15≈25 inches; H11≈8.5 inches; H12≈2.75 inches; H13≈2 inches; H14≈2.75 inches; H15≈2 inches; H16≈2.75 inches; H17≈2.25 inches; H18≈3 inches; and H19≈3.75 inches.

In the illustrated embodiment, the intersection of the lower edge of the first strap 410 with the left side of the central body portion 402, the intersection of the upper edge of the second strap 412 with the left side of the central body portion and the intersections of the upper edge and the lower edge of the third strap 414 with the right side of the central body portion are rounded with fillets 420. In addition, the intersection of the upper edge of the first strap with the top of the central body portion and the intersection of the lower edge of the second strap with the bottom of the central body portion are curved with fillets 422. As discussed above, the fillets function to inhibit tearing of the sheet 400 when the straps and the central body portion are stretched as discussed below. Preferably, the outer vertices of the three straps and upper right and lower left vertices of the central body portion are also rounded. In preferred embodiments, the outer edges of the sheet 400 defining the central body portion and the straps and the inner edge of the sheet defining the hole 404 are reinforced as described above.

The obverse (hidden) surface of the first strap 410 of the knee compression wrap 312 has a generally rectangular section 430 of the hook portion of a hook and loop fastening system positioned proximate to the left end. The rectangular hook section is secured thereon by gluing, by stitching or by another suitable method. The obverse surface of the second strap 412 of the knee compression wrap has a generally rectangular section 432 of the hook portion of a hook and loop fastening system positioned proximate to the left end. The rectangular hook section is secured thereon by a suitable method. The obverse surface of the third strap 414 of the knee compression wrap has a generally rectangular section 434 of the hook portion of a hook and loop fastening system positioned proximate to the right end. The rectangular hook section is secured thereon by a suitable method.

The exposed side of the central body portion has three generally rectangular sections of the loop portions of hook and loop fastening systems positioned proximate the left side of the central body portion. An upper loop section 440 is generally aligned with the hook section 440 on the first strap 410. A lower loop section 442 is generally aligned with the hook section 432 on the second strap 412. A middle loop section 444 is generally aligned with the hook section 434 on the third strap 414.

The exposed side of the second strap 362 has a generally rectangular section 366 (shown in hidden lines) of the hook portion of a hook and loop fastening system secured thereon by a suitable method. In the illustrated embodiment, the rectangular section of the loop portion is wider than the rectangular section of the hook portion to allow the engagement to be adjusted, as discussed below.

The knee compression wrap 312 functions similarly to the hip compression wrap 310. After filling the ice bag 100 with ice and inserting the neck portion 116 of the ice bag through the hole 404, the cap 140 is attached and the air release button 210 is depressed to release air in the ice bag. The bottom portion 112 of the ice bag is positioned against the person's knee. The third strap 414 is stretched behind the person's knee, and the hook section 434 proximate to the end of the third strap is engaged with the middle loop section 444 on the central body portion 402. The first strap 410 is stretched around the person's leg above the knee, and the hook section 430 proximate to the end of the first strap is engaged with the upper loop section 440 on the central body portion. The second strap 412 is stretched around the person's leg below the person's knee, and the hook section 432 proximate to the end of the second strap is engaged with the lower loop section 442 on the central body portion.

When secured as described above, the first strap 410, the second strap 412 and the third strap 414 of the knee compression wrap 312 allow the person's knee to flex comfortably. In particular, the first strap and the second strap are positioned sufficiently far apart that the material between the two straps stretches to accommodate the additional distance when the flexure of the lower leg moves the second strap farther away from the first strap. At the same time, the independently secured third strap retains the center of the central body portion 402 with the hole 404 in the correct position over the knee.

The knee compression wrap 312 applies pressure to force the bottom portion 112 of the ice bag 100 against the person's knee. As the ice within the ice bag melts, the air release button 210 is depressed to release the air originally entrapped within the ice so that pressure is maintained against the ice in the ice bag.

Although described as a knee compression wrap, the compression wrap 312 can be adapted to provide compression and heat removal for other body parts. For example, the dimensions of the knee compression wrap are easily reduced and the proportions adjusted as needed to provide a compression wrap for a person's elbow, wrist, ankle, foot or other body part. For smaller joints and other body parts, the size of the ice bag 100 may also be reduced in order to concentrate the pressure and heat removal on the smaller body parts.

Figure 14:
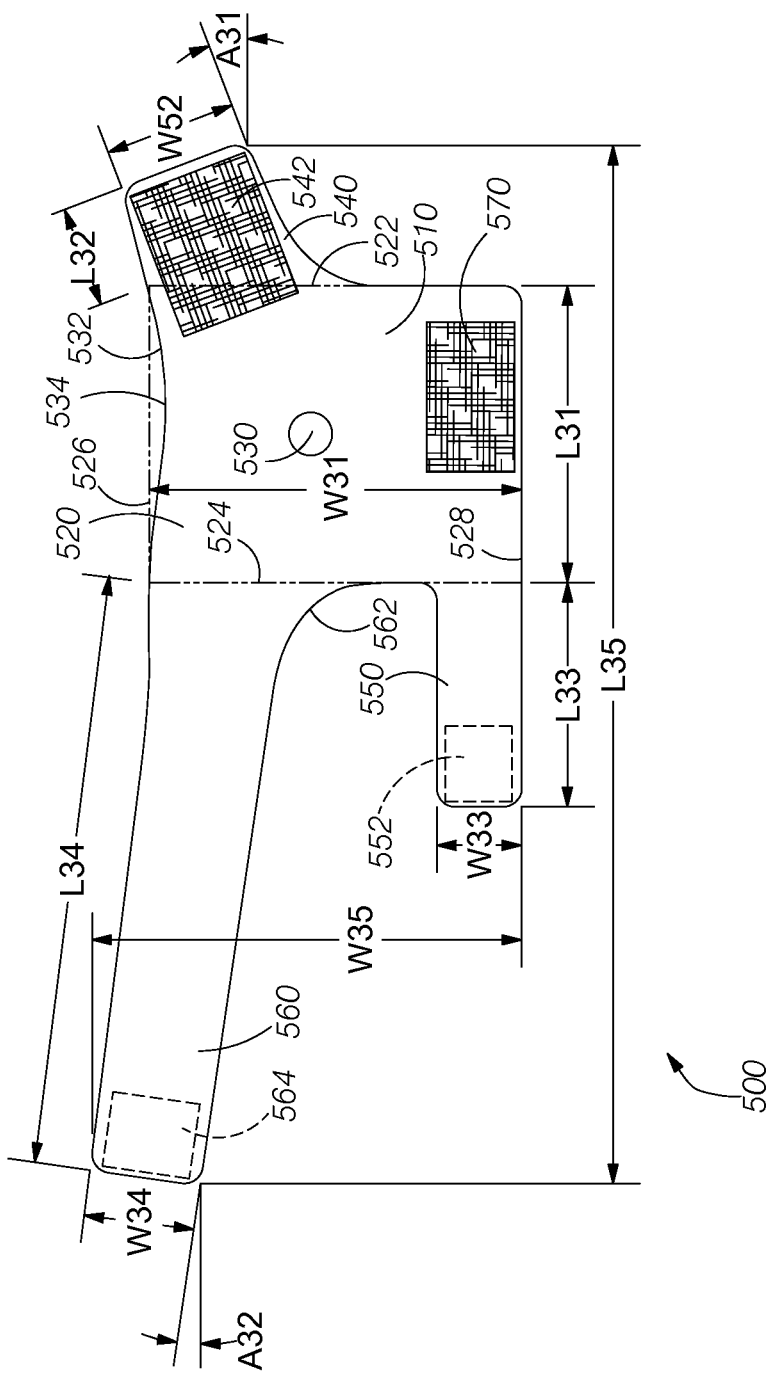
FIG. 14 illustrates a plan view of a compression wrap for securing the ice bag of FIGS. 1-11 to a person's left shoulder.
Figure 15:
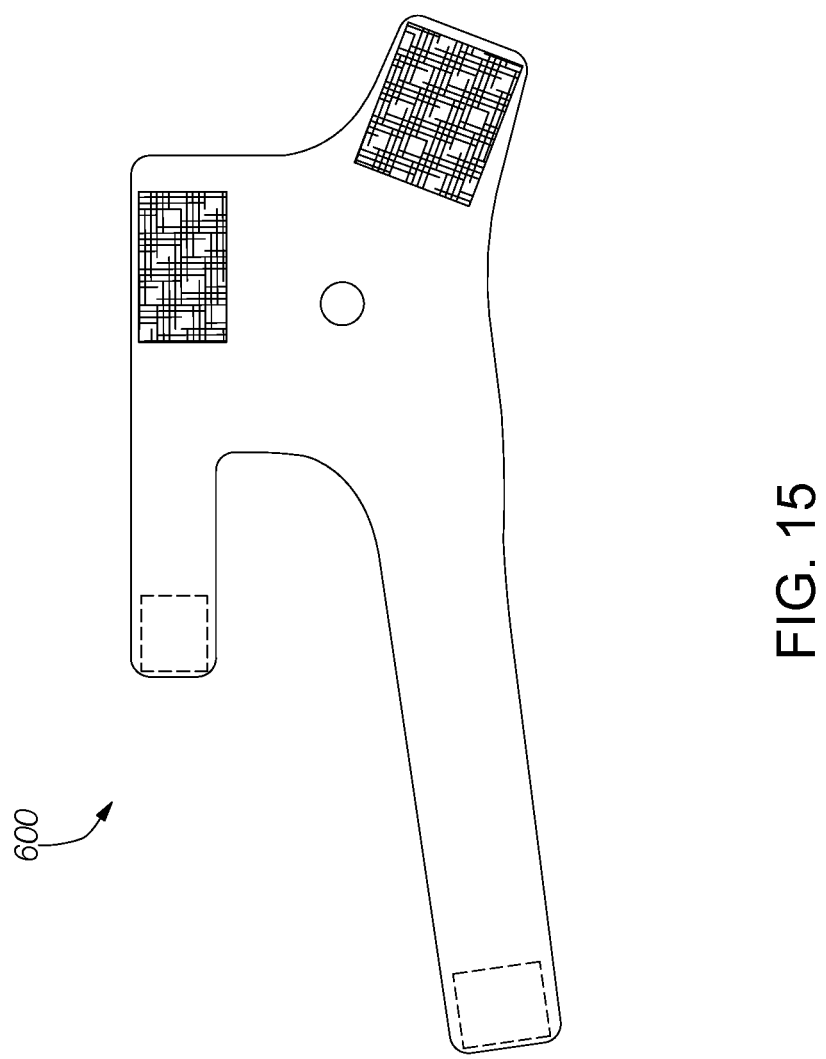
FIG. 15 illustrates a plan view of a compression wrap for securing the ice bag of FIGS. 1-11 to a person's right shoulder.

FIG. 14 illustrates an embodiment of a shoulder compression wrap 500 for applying a single ice bag 100 of FIGS. 1-11 to the left shoulder of a person. A corresponding embodiment 600 for the right shoulder is shown in FIG. 15.

As used in the following description, horizontal and vertical refer to the landscape orientation of the embodiment in FIG. 14.

The shoulder compression wrap 500 of FIG. 14 comprises a single integral sheet 510 of L-foam neoprene or other suitable material formed in the pattern shown in FIG. 14. Preferably, the shoulder compression wrap comprises material having a thickness of approximately 5 millimeters to provide greater strength over a larger surface area.

The sheet 510 includes a includes a central body portion 520 that is generally formed with multiple curves to allow the compression wrap to be positioned comfortably on the person's shoulder proximate to the person's neck and to allow the compression wrap to be stretched without tearing the material. In the illustrated embodiment, in the absence of the various curves and fillets, the central body portion has a generally rectangular shape as generally outlined by a set of phantom lines defining a right edge 522, a left edge 524, an upper edge 526 and a lower edge 528. The central body portion has a length L31 defined generally between the right edge and the left edge; and has a width W31 defined generally between the upper edge and the lower edge. The phantom outline is for descriptive purposes only and does not represent actual boundaries of the central body portion of the compression wrap. The central body portion and the straps described below are formed from a continuous sheet such that no well-defined boundaries exist where the central body portion transitions to the straps.

The central body portion 520 includes a hole 530 located within a central region of the central body portion. The hole receives the neck portion 116 of the ice bag as described above. When secured to a person as described below, the ice bag is positioned generally on top of the person's left shoulder. In the illustrated embodiment, the hole has a diameter of approximately 1.75 inches. An upper physical edge 532 of the center body portion includes a smooth curved indentation 534 (relative to the phantom upper edge 526) to provide clearance around the person's neck when the compression wrap 500 is secured to the person's left shoulder so that the otherwise straight edge of the compression wrap is not applied against the person's neck.

A first strap 540 extends upward and to the right from an upper portion of the right edge 522 of the central body portion 520 at an angle A31 of approximately 21 degrees with respect to horizontal. The first strap has a length L32 and a width W32. A first generally rectangular section 542 of a loop portion of a hook and loop fastening system is positioned on the first strap in general alignment with the direction of the length of the first strap. A portion of the rectangular section of the loop portion may extend onto the central body portion as shown. The rectangular section is secured to the first strap and the central body portion by a suitable method as discussed above with respect to the other embodiments.

A second strap 550 extends to the left from a lower portion of the left edge 524 of the central body portion 520. The second strap is generally horizontal with the lower edge of the second strap generally aligned with the lower edge 528 of the central body portion. In the illustrated embodiment, the second strap has a length L33 and a width W33. A first generally rectangular section 552 of a hook portion (shown in hidden lines) of a hook and loop fastening system is positioned on the obverse (hidden) side of the second strap near the left end of the second strap and in general alignment with the direction of the length of the second strap. The rectangular hook portion section is secured to the second strap by a suitable method as discussed above.

A third strap 560 extends up and to the left from an upper portion of the left edge 524 of the central body portion 520 at an angle A32 of approximately 8 degrees with respect to horizontal. The third strap has a length L34 and a width W34. The lower edge of the third strap transitions to the central body portion via a large curved fillet section 562 to avoid creating a sharp intersection with the central body portion. A second generally rectangular section 564 of a hook portion (shown in hidden lines) of a hook and loop fastening system is positioned on the obverse (hidden) side of the third strap near the left end of the third strap and in general alignment with the direction of the length of the third strap. The second rectangular hook section is secured to the third strap by a suitable method as discussed above.

A second generally rectangular section 570 of the loop portion of a hook and loop fastening system is positioned on the central body portion 520 between the hole 530 and the lower edge 528 of the central body portion. In the illustrated embodiment, the second loop portion section is oriented with a longer side generally parallel to the lower edge of the central body portion.

As illustrated, prior to stretching, the left shoulder compression wrap 500 has an overall width W35 and an overall length L35.

The dimensions of the left shoulder compression wrap 500 can be varied in accordance with ranges of sizes of persons for whom the shoulder compression wrap is intended. For example, in one exemplary embodiment, the widths and heights have the following approximate dimensions prior to stretching of the shoulder compression wrap: W31≈15 inches; W32≈5.3 inches; W33≈3.4 inches; W34≈4.7 inches; W35≈17.4 inches L31≈12 inches; L32≈4.1 inches; L33≈9.1 inches; L34≈24 inches; and L35≈42 inches. In view of the elasticity of the neoprene sheet 510, the foregoing dimensions can vary. Furthermore, the relative lengths and widths of the straps and the central body portion can have different proportions than the exemplary dimensions.

Figure 19:
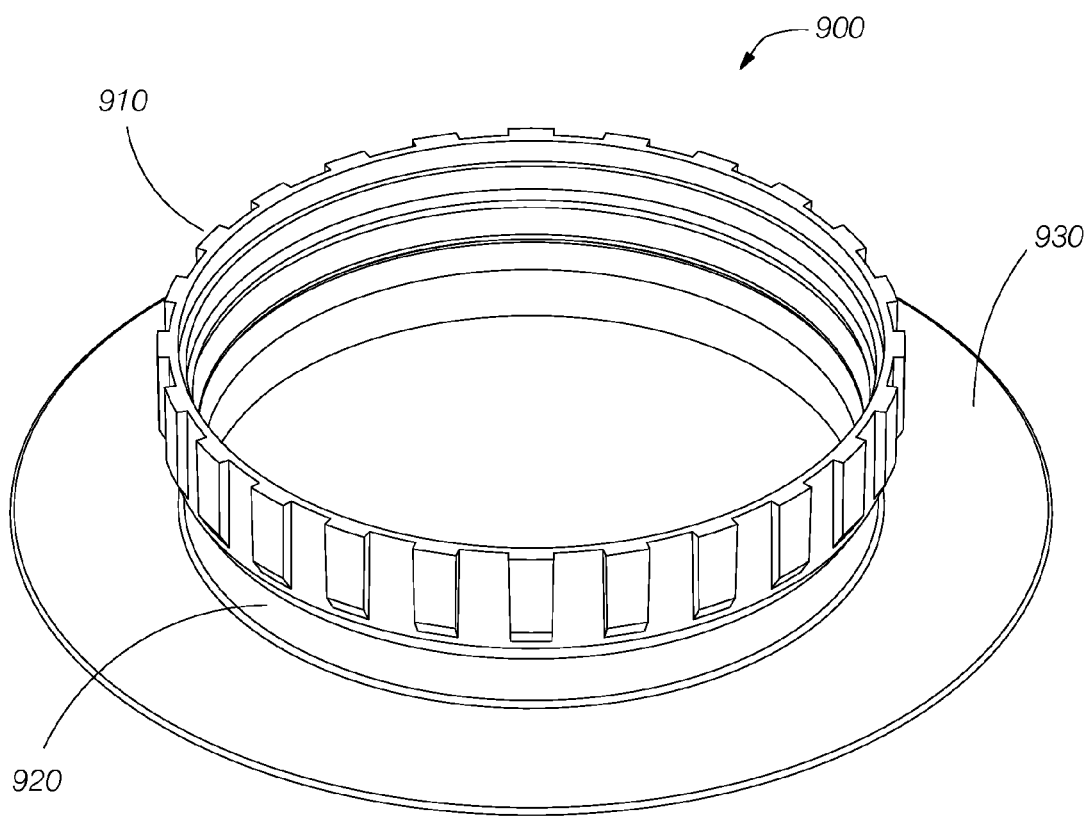
FIG. 19 illustrates a perspective view of an alternative embodiment of the outer collar ring of FIGS. 1-5 in which the outer collar ring includes a flange to further secure the ice bag with the compression wraps of FIGS. 12-16

The left shoulder compression wrap 500 of FIG. 19 is used with the ice bag 100 of FIGS. 1-11 to apply pressure to and to extract heat from the person's left shoulder. After filling and closing the ice bag 100, the cap 140 and neck portion 116 of the ice bag are pushed through the hole 530 in the compression wrap. The ice bag is then positioned on the top of the person's left shoulder with the body portion 520 generally on top of the person's left shoulder such the end of the first strap 540 is draped over the back of the person's left shoulder and such that the end of the second strap 550 is draped over the front of the person's left shoulder. The second strap is stretched to pass beneath the person's left underarm so that the first hook portion section 552 on the end of the second strap is positioned to engage the second loop portion section 570 on the body portion. The third strap 560 is then stretched and pulled across the person's chest, around the person's right side and back across the person's upper back until the second hook section 564 on the free end of the third strap is positioned for engagement with the first loop portion section 542 on the first strap. It should be understood that since the central body portion and the three straps comprise a single integral sheet of neoprene, the entire shoulder compression wrap stretches to allow each hook portion section to engage the respective loop portion section. The curves and fillets on the central body portion proximate the straps allow the central body portion to stretch without tearing as might happen if the central body portion were to be formed with sharp corners. Preferably, the outer edges of the sheet 510 defining the central body portion and the straps and the inner edge of the sheet defining the hole are advantageously reinforced as describe above.

The compression wrap 500 can be worn on the shoulder for extended periods without requiring readjustment of the straps. In particular, as the ice melts within the ice bag 100, the entrapped air released from the ice enters the ice bag and creates a volume of air that acts as a cushion to diffuse the pressure applied against the ice bag. When the user senses that the pressure applied by the ice bag is lower, the user simply depresses the air release button 210, as described above. The air release button is easily accessible at the top of the person's shoulder. The tension in the stretched straps 540, 550, 560 and central body portion 520 of the compression wrap causes the compression wrap to shrink and force the air out of the ice bag thus removing the cushioning effect caused by the air. The user again benefits from the pressure applied directly against the ice bag and thus against the user's shoulder.

FIG. 15 illustrates a right shoulder compression wrap 600, which is the mirror image of the left shoulder compression wrap 500 of FIG. 14. The right shoulder compression wrap is constructed in the same manner as described above and operates in the same manner as the left shoulder compression wrap. Accordingly, the foregoing description applies to FIG. 15 except for the references to left and right.

Figure 16:
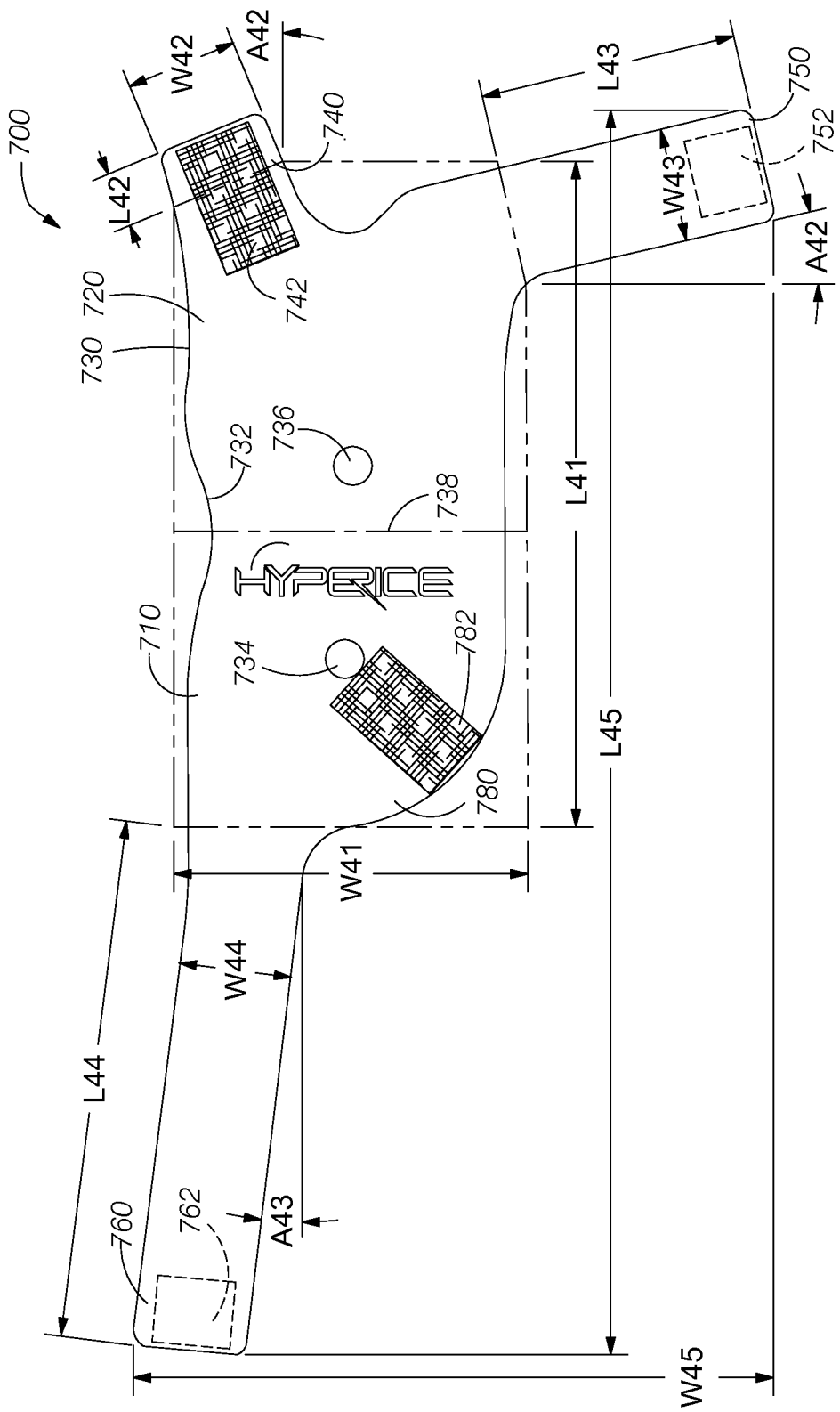
FIG. 16 illustrates a plan view of a compression wrap for securing a first ice bag of FIGS. 1-11 to the front of a person's left shoulder and for securing a second ice bag of FIGS. 1-11 to the back of the person's left shoulder.

FIG. 16 illustrates an embodiment of a shoulder compression wrap 700 for applying two of the ice bags 100 of FIGS. 1-11 to the left shoulder of a person. A corresponding embodiment 800 for the right shoulder is shown in FIG. 18. Unlike the single ice bag shoulder compression wrap 500 of FIG. 14, which positions the ice bag on top of the person's shoulder, the shoulder compression wrap of FIGS. 16 and 17 positions a first ice bag over a forward portion of the shoulder and positions a second ice bag over a rearward portion of the shoulder. The pressure applied to the two ice bags by the single compression wrap squeezes the shoulder between the two ice bags to enhance the pressure applied to the shoulder and to assure thermal transfer of heat from the shoulder to the ice bags.

As used in the following description, horizontal and vertical refer to the landscape orientation of the embodiment in FIG. 16.

The shoulder compression wrap 700 of FIG. 16 comprises a single integral sheet 710 of L-foam neoprene or other suitable material formed in the pattern shown in FIG. 16. Preferably, the shoulder compression wrap comprises material having a thickness of approximately 5 millimeters to provide greater strength over a larger surface area.

The sheet 710 includes a includes a central body portion 720 that is generally formed with multiple curves to allow the compression wrap to be positioned comfortably on the person's shoulder proximate to the person's neck and to allow the compression wrap to be stretched without tearing the material. In the illustrated embodiment, in the absence of the various curves and fillets, the central body portion has the general shape of a six-sided polygon as indicated by a phantom outline 722. As discussed above, the phantom outline is for descriptive purposes only and does not represent actual boundaries of the compression wrap. Prior to stretching of the material, the central body portion has a width W41 at the left end in FIG. 16 and a length L41.

An upper edge 730 of the central body portion 720 has an indentation 732 formed therein to accommodate placement of the upper edge proximate to a person's neck. The central body portion further includes a first hole 734 and a second hole 736, each of which has a diameter of approximately 1.75 inches in the illustrated embodiment. The first hole is positioned to the left of a reference line 738 and the second hole is positioned to the right of the reference line. The reference line extends approximately from the midpoint of the indentation and is shown for descriptive purposes only. When the compression wrap 700 is positioned on a person's left shoulder with the indentation positioned proximate the person's neck, the reference line would be generally aligned with the top of the person's shoulder with the first hole being positioned on the front of the person's shoulder above the person's chest and with the second hole positioned on the rear of the person's shoulder on the person's upper back. When lying flat as shown in FIG. 16, the first hole and the second hole are spaced apart by approximately 9 inches.

The upper portion of the right edge of the central body portion transitions to a first strap 740. The first strap is generally oriented upward and to the right at an angle A41 of approximately 25 degrees with respect to horizontal. In the illustrated embodiment, the first strap has a width W42 and a length L42 (measured from the boundary of the phantom outline). A generally rectangular section 742 of a loop portion of a hook and loop fastening system is positioned on the first strap in general alignment with the direction of the length of the first strap. The rectangular section of the loop portion extends onto the central body portion as shown. The rectangular section is secured to the first, short strap and the central body portion by a suitable method as discussed above with respect to the other embodiments.

The right portion of the lower edge of the central body portion 720 transitions to a second strap 750. The second strap is generally oriented down and to the right at an angle A42 of approximately 15 degrees with respect to vertical. In the illustrated embodiment, the second strap has a width W43 and a length L43 (measured from the boundary of the phantom outline). A generally rectangular section 752 of a hook portion (shown in hidden lines) of a hook and loop fastening system is positioned on the obverse (hidden) side the second strap in general alignment with the direction of the length of the second strap. The rectangular hook section is secured to the second strap by a suitable method as discussed above.

The upper portion of the left edge of the central body portion transitions to a third strap 760. The third strap is generally oriented up and to the left at an angle A43 of approximately 7 degrees with respect to horizontal. In the illustrated embodiment, the third strap has a width W44 and a length L44 (measured from the boundary of the phantom outline). A generally rectangular section 762 of a hook portion (shown in hidden lines) of a hook and loop fastening system is positioned on the obverse (hidden) side the third strap in general alignment with the direction of the length of the third strap. The rectangular hook section is secured to the third strap by a suitable method as discussed above.

A lower left corner portion 780 of the central body portion 720 is formed as a large curve. A generally rectangular section 782 of a loop portion of a hook and loop fastening system is positioned on the lower left corner portion and is oriented at approximately 45 degrees to the horizontal along a radius extending from the approximate midpoint of the curve forming the corner portion. The rectangular section is secured to the central body portion by a suitable method as discussed above.

As illustrated, prior to stretching, the shoulder compression wrap 700 has an overall width W45 and an overall length L45.

The dimensions of the shoulder compression wrap 700 can be varied in accordance with ranges of sizes of persons for whom the shoulder compression wrap is intended. For example, in one exemplary embodiment, the widths and heights have the following approximate dimensions: W41≈16 inches; W42≈5 inches; W43≈5 inches; W44≈5 inches; W45≈29 inches; L41≈30.25 inches; L42≈2.5 inches; L43≈11.75 inches; L44≈23.5 inches; and L45≈56.75 inches. In view of the elasticity of the neoprene sheet 710, the foregoing dimensions can vary. Furthermore, the relative lengths and widths of the straps and the central body portion can have different proportions than the exemplary dimensions.

Figures 17A, 17B:
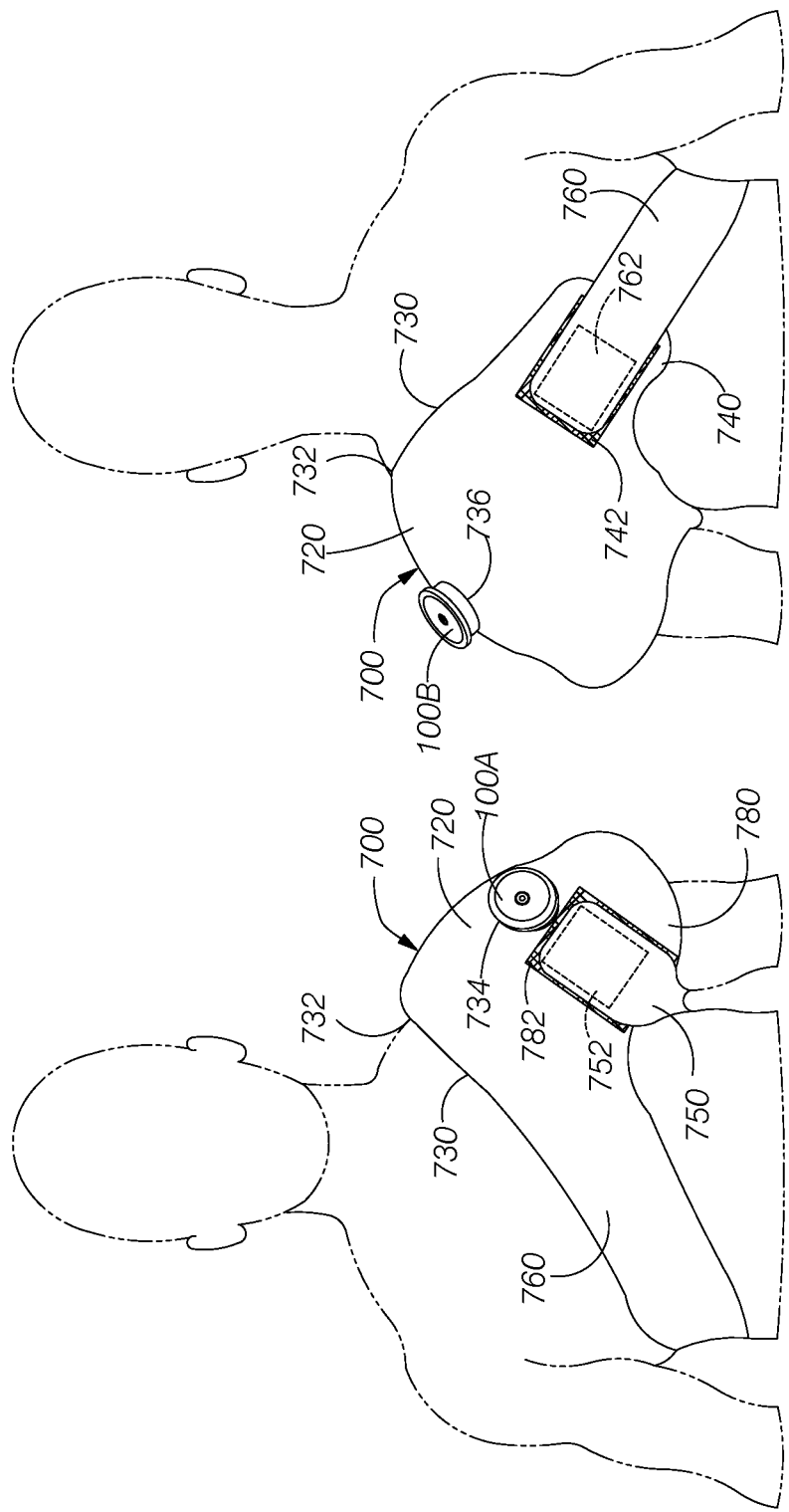

As illustrated in FIGS. 17A and 17B, the shoulder compression wrap 700 of FIG. 16 is used by filling a first ice bag 100A and a second ice bag 100B with ice and positioning the respective neck 210 of the first ice bag through the first hole 734 in the central body portion 720 and positioning the respective neck of the second ice bag through the second hole 736 in the central body portion. The volume of ice in each ice bag may be adjusted as desired by the user. The first ice bag is positioned in front of the person's left shoulder above the person's chest, and the second ice bag is positioned behind the person's left shoulder on the person's upper back. As discussed above, the indentation 732 is positioned along the person's neck. In general, the compression wrap is draped on the person's left shoulder such that the reference line 738 would be along the top of the person's shoulder.

While holding the two ice bags 100 in the selected positions in front of and behind the person's shoulder, the second strap 750 is pulled beneath the person's left underarm and is stretched until the hook section 752 on the free end of the second strap is positioned for engagement with the loop section 782 on the lower left corner portion 780 of the central body portion 720. The third strap 760 is then stretched and pulled across the person's chest, around the person's right side and back across the person's upper back until the hook section 762 on the free end of the third strap is positioned for engagement with the loop section 742 on the first strap 740. It should be understood that since the central body portion and the three straps comprise a single integral sheet of neoprene, the entire shoulder wrap stretches to allow each hook section to engage the respective loop section. The large curves on the central body portion proximate the straps allow the central body portion to stretch without tearing as might happen if the central body portion were to be formed with sharp corners. The outer edges of the sheet 710 and the edges of the sheet around the holes 734, 736 are advantageously reinforced as describe above.

When the two ice bags 100A, 100B are positioned as shown in FIGS. 17A and 17B, the bottom portions of the ice bags form an upside-down V-shape with the vertex of the "V" positioned at the top of the shoulder in the region around the clavicle and the acromioclavicular (AC) joint.

The compression wrap 700 can be worn on the shoulder for extended periods without requiring readjustment of the straps. In particular, as the ice melts within the ice bags 100, the entrapped air released from the ice enters the ice bags and creates respective volumes of air that act as cushions to diffuse the pressure applied against the ice bags. When the user senses that the pressure applied between the two ice bags is lower, the user simply depresses the air release button 210 on each ice bag, as described above. The air release buttons are easily accessible near the top of the person's shoulder. The tension in the stretched straps and central body of the compression wrap causes the compression wrap to shrink and force the air out of the ice bags thus removing the cushioning effect caused by the air. The user again benefits from the pressure applied directly against the ice bags and thus against the user's shoulder.

FIG. 18 illustrates a right shoulder compression wrap 800, which is the mirror image of the left shoulder compression wrap 700 of FIG. 16. The right shoulder compression wrap is constructed in the same manner as described above and operates in the same manner as the left shoulder compression wrap. Accordingly, the foregoing description applies to FIG. 18 except for the references to left and right.

FIG. 19 illustrates an outer collar ring 900 in accordance with a further embodiment in which the outer collar ring includes an upper portion 910, which corresponds to the outer collar ring 122 of FIGS. 1-5. The outer collar ring in FIG. 19 further includes an extended cylindrical lower portion 920 which supports a flange 930. As illustrated, the flange has a diameter that is substantially larger than the cylindrical lower portion and is larger than the upper gripping portion 142 of the cap 140 of the ice bag 100. Although the respective holes in the compression wraps of FIG. 11-20 are intended to stretch to accommodate upper gripping portion of the cap and the outer ring of the ice bag 100 and then shrink to provide a snug fit around the neck portion 116 of the ice bag, the elasticity of the portion of the compression wrap surrounding the hole may not always be sufficient to cause the hole to shrink to a sufficiently small diameter to securely retain the neck portion of the ice bag. In other cases, the elasticity of the hole may be too great and may cause the material surrounding the hole to apply too much pressure to the flexible neck portion of the ice bag. The extended cylindrical lower portion provides a solid barrier to preclude closure of the neck portion of the ice bag. The flange provides a large surface area that is much less likely to pass through the hole in the compression wrap even when the hole does not shrink to a sufficiently small diameter after upper gripping portion of the cap of the ice bag is inserted through the hole.

As various changes could be made in the above constructions without departing from the scope of the invention, it is intended that all the matter contained in the above description or shown in the accompanying drawings shall be interpreted as illustrative and not in a limiting sense.

What is claimed is:

1. A system that simultaneously applies compression and cooling to a body part of a person, comprising:
   an ice bag having a removable cap for inserting ice into and removing water from the ice bag;
   an air release system in the removable cap that allows release of air from the ice bag without removing or loosening the removable cap, wherein:
      the removable cap comprises an outer surface and an inner surface, and further comprises a hole formed through the removable cap between the outer surface and the inner surface;
      the air release system comprises an elastic plug positioned through the hole in the removable cap, the elastic plug including a flange positioned against the inner surface of the removable cap and blocking access to the hole; and
      an air release button is positioned in the elastic plug, the air release button comprising an upper actuator that is movable toward the upper surface of the removable cap and comprising an extended portion that extends from the upper actuator into the elastic plug, the extended portion having a lower end that forces the flange of the elastic plug away from the inner surface of the removable cap to allow air to be released through the hole in the removable cap; and a compression wrap comprising a unitary sheet of elastic material having a central body with straps extending therefrom, the central body including a hole that receives a neck of the ice bag, the straps positionable with respect to the body part of the person to secure the ice bag over the body part to apply pressure to the body part and to transfer heat from the body part to the ice within the ice bag, wherein the air release valve in the removable cap allows air to be released from the ice bag without disturbing the compression wrap or the removable cap, and wherein the compression wrap contracts to compensate for a volume of the released air, thereby maintaining continuous pressure on and thermal contact with the body part.

2. The system as defined in claim 1, wherein the straps extending from the central body of the compression wrap include at least a first strap that extends from a first side of the central body in a first direction and at least a second strap that extends from a second side of the central body in a second direction.

3. The system as defined in claim 1, wherein the straps extending from the central body of the compression wrap include at least a first strap sized and positionable to secure an upper portion of the central body to a waist of the person and include at least a second strap sized and positionable to secure a lower portion of the central body to a leg of the person, the central body thereby being positionable over a hip of the person to position the ice bag in contact with the hip of the person to cause the central body to apply pressure to the ice bag.

4. The system as defined in claim 1, wherein the straps extending from the central body of the compression wrap include at least a first strap sized and positionable to secure an upper portion of the central body to a shoulder of the person proximate to one side of a neck of the person, and include at least a second strap sized and positionable to secure a lower portion of the central body to an arm of the person, the central body thereby being positionable over the shoulder of the person to position the ice bag in contact with the shoulder of the person to cause the central body to apply pressure to the ice bag.

5. The system as defined in claim 1, wherein the ice bag comprises medical grade latex having a thickness of approximately 0.015 inch.

6. The system as defined in claim 5, wherein the medical grade latex is leached to remove proteins that cause allergic reactions and is blended with an antimicrobial solution.

7. An ice bag, comprising:
a flexible container having an inner cavity for receiving a volume of ice, the flexible container having at least one surface for placement against a portion of a body to be cooled;
an opening in the flexible container to provide access to the inner cavity;
an engagement device on the flexible container proximate to the opening, the engagement device having a first mating engagement system; and
a removable cap having an inner surface and an outer surface, the removable cap having a second mating engagement system engageable with the first mating engagement system to secure the removable cap in sealing engagement with the first mating engagement system of the engagement device to seal the ice bag, the removable cap including an air release system to release air from the ice bag while the second mating engagement system of the removable cap is maintained in sealing engagement with the first mating engagement system of the engagement device, wherein the air release system comprises:
a bore formed through the removable cap between the outer surface of the removable cap and the inner surface of the removable cap; and
a plug positioned with respect to the bore in the removable cap, the plug comprising:
a lower sealing portion positioned on the inner surface of the removable cap, the lower sealing portion having a resting state that blocks the bore and precludes release of the air through the bore;
an upper portion positioned on the outer surface of the removable cap;
an elastic portion between the upper portion and the lower sealing portion, the elastic portion being sized to secure the lower sealing portion against the inner surface of the removable cap; and
a release mechanism positioned in the plug and extending into the elastic portion of the plug toward the lower sealing portion, the release mechanism having an upper actuator accessible at the upper portion of the plug, the release mechanism responsive to pressure applied to the upper actuator to force the lower sealing portion to move to a displaced state away from the inner surface of the removable cap to allow air to pass through the bore, the elastic portion returning the lower sealing portion to the resting state when the pressure applied to the upper actuator is removed.

8. The ice bag as defined in claim 7, wherein the flexible container comprises medical grade latex having a thickness of approximately 0.015 inch.

9. The ice bag as defined in claim 8, wherein the medical grade latex is leached to remove proteins that cause allergic reactions and is blended with an antimicrobial solution.

10. The ice bag as defined in claim 7, wherein the flexible container has a bottom disposed opposite the opening that is positionable against a body portion to be cooled, and wherein the bottom has a generally rectangular surface.

11. The ice bag as defined in claim 10, wherein the generally rectangular surface is square.

* * * * *